(12) United States Patent
Carver et al.

(10) Patent No.: US 8,633,289 B2
(45) Date of Patent: Jan. 21, 2014

(54) FORMATION OF [2,2]PARACYCLOPHANE AND RELATED COMPOUNDS AND METHODS FOR THE FORMATION OF POLYMERS FROM CYCLOPHANES

(75) Inventors: David R. Carver, Colorado Springs, CO (US); Sean W. Reynolds, Colorado Springs, CO (US)

(73) Assignee: Carver Scientific, Inc., Baton Rouge, LA (US)

( * ) Notice: Subject to any disclaimer, the term of this patent is extended or adjusted under 35 U.S.C. 154(b) by 0 days.

(21) Appl. No.: 13/599,996

(22) Filed: Aug. 30, 2012

(65) Prior Publication Data

US 2013/0109827 A1    May 2, 2013

Related U.S. Application Data

(60) Provisional application No. 61/529,436, filed on Aug. 31, 2011.

(51) Int. Cl.
*C08F 136/02*    (2006.01)
*C07C 41/00*    (2006.01)
*C07C 17/00*    (2006.01)
*C07C 1/00*    (2006.01)

(52) U.S. Cl.
USPC ......... 526/340.3; 568/633; 570/190; 585/320

(58) Field of Classification Search
USPC ......... 526/340.3; 568/633; 570/190; 585/320
See application file for complete search history.

(56) References Cited

U.S. PATENT DOCUMENTS

| | | |
|---|---|---|
| 3,342,754 A | 9/1967 | Gorham |
| 3,616,314 A | 10/1971 | Settineri et al. |
| 3,907,748 A | 9/1975 | Marvel et al. |
| 4,359,327 A | 11/1982 | Armand et al. |
| 4,500,562 A | 2/1985 | Jahn et al. |
| 4,532,369 A | 7/1985 | Hartner |
| 4,675,462 A | 6/1987 | Ungarelli et al. |
| 4,734,533 A | 3/1988 | Ungarelli et al. |
| 4,769,505 A | 9/1988 | Lee et al. |
| 4,795,838 A | 1/1989 | Bornengo et al. |
| 4,806,702 A | 2/1989 | Lee et al. |
| 4,816,608 A | 3/1989 | Bornengo et al. |
| 4,849,559 A | 7/1989 | Lee et al. |
| 4,853,488 A | 8/1989 | Ungarelli et al. |
| 4,886,923 A | 12/1989 | Ungarelli et al. |
| 5,110,903 A | 5/1992 | Lee et al. |
| 5,266,291 A * | 11/1993 | Drnevich et al. ............. 423/392 |

OTHER PUBLICATIONS

Modern Cyclophane Chemistry, Editors: Rolf Gleiter Henning Hopf, John Wiley (2004).

* cited by examiner

*Primary Examiner* — William Cheung
(74) *Attorney, Agent, or Firm* — Mark Young, P.A.

(57) ABSTRACT

An improved process and method for the formation of stable intermediate cyclophanes. Embodiments describe a general method for the production of substituted and unsubstituted cyclophanes. The components include a pyrolysis reaction tube that may be electrically heated into which a flowing stream of nitrous oxide with xylene vapor in an optional inert carrier gas at atmospheric pressure. The exit gas is condensed resulting in the deposition of [2,2']paracyclophane. Additionally a process and method whereby the reactive intermediates of the reaction described above can be directly deposited and polymerized at atmospheric pressures or thereabout is disclosed.

12 Claims, 2 Drawing Sheets

FORMATION OF [2,2]PARACYCLOPHANE AND RELATED COMPOUNDS AND METHODS FOR THE FORMATION OF POLYMERS FROM CYCLOPHANES

FIELD OF THE INVENTION

The present invention relates to the field of synthesis of cyclophanes and their method of application and utility as polymer precursors.

BACKGROUND OF THE INVENTION

Cyclophanes are a subset of organic structures that are well known and characterized. Several excellent reviews and books have been published that cover the methods and applications very well.

Briefly, cyclophanes and other related benzocycloid compounds are organic molecules that have structures where a cyclic carbon or heteroatom substituted chain is attached to two or more positions of an aromatic ring. The term cyclophanes is used to describe compounds that have a relationship or a structure that broadly fits into this structural category.

One of the more highly researched cyclophane compounds is the paracyclophane structure. In one set of cyclophane compounds (as shown in the structures of [n]metacyclophanes (I), [n]paracyclophanes (II) and [n,n']cyclophanes below), we see structure III as a general structure for paracyclophanes.

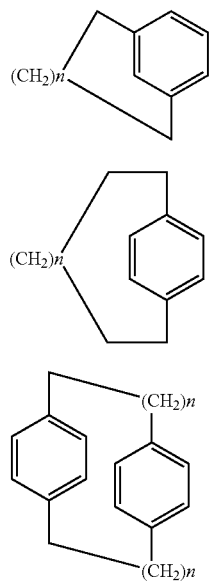

In this substitution pattern we note that the simplest member of the series is where n=1. In this case the molecule is named [2,2']paracyclophane. This molecule and derivatives thereof are an important class of compounds that are able to form a variety of polymer structures. For this reason they are highly desirable organic intermediates that have been used as precursors for conformal coatings for numerous applications. In these applications the molecule shown in III (n=1) is normally heated in a vacuum to produce a significant vapor pressure and to force a disassociation of the molecule into a highly reactive intermediate. This pyrolytic cleavage of the [2.2°]paracyclophane results in two molecules of the reactive intermediate p-xylylene (shown below).

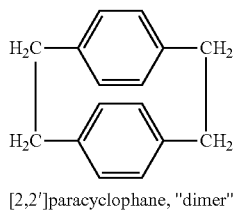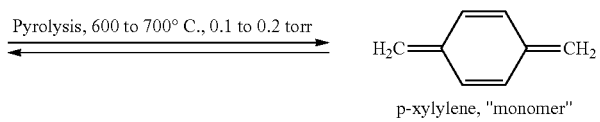

[2,2']paracyclophane, "dimer"    p-xylylene, "monomer"

Additionally, the reactive intermediate p-xylylene may be formed from the "dimer" by utilization of a pyrolysis discharge under reduced atmospheric pressure. (ref. Gorham U.S. Pat. No. 3,342,754). This procedure has commonly been called the "Gorham process".

As the structure indicated, the reactive intermediate, p-xylylene is a long-lived intermediate species that has the ability to react to form a highly desirable polymer. In particular this polymer is a conformal coating that has the ability to coat surfaces in relatively uniform layers that are highly resistant to chemical solvents, gases, and biological attack. The p-xylylene is deposited in a vacuum onto a target surface for conformal coating. On the surface it reforms into a repeating unit of poly(p-xylylene), also known as parylene. In the case of no substituents in the aromatic ring or the aliphatic side-chains other than hydrogen, this polymer compound is called parylene-N.

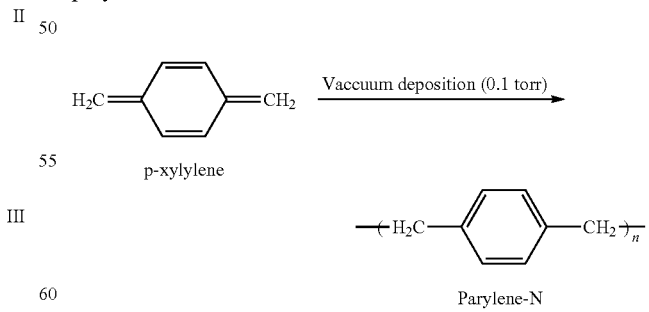

Para-xylylene, as a valuable reactive intermediate, has had its synthesis primarily through the pyrolysis of [2,2']paracyclophane. Thus, the synthesis of [2,2']paracyclophane is a critical stable intermediate in the utilization of p-xylylene and the polymer parylene.

Synthesis of [2,2']paracylophane is through the route of the 1,6-Hofmann elimination of quaternary ammonium salts.

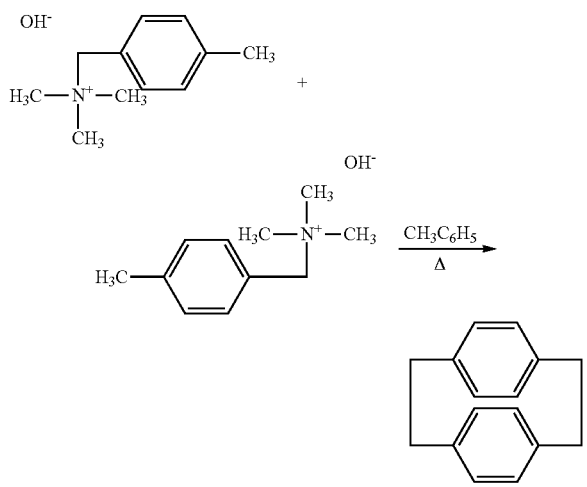

This route going through a quaternary ammonium salt, although widely used, suffers from several drawbacks. The paracylophane is usually produced in low yields using a multi-step processes.

Additionally, due to the low yield and large amount of side-products, extensive purification of the resultant dimer is an additional process procedure.

SUMMARY OF THE INVENTION

Heretofore, the restriction of the known vacuum process for both the pyrolysis of the dimer and the deposition of the monomer to produce the polymer has increased the cost and limited the utility of the polymer's applications.

A variety of substitutions for the various hydrogen atoms and substitution of heteroatoms in place of the various carbon atoms in the rings and chains have been made. It would be desirable to have an efficient and effective method for the formation of these compounds, both known and unknown.

Thus, there is a need for an improved synthesis of the stable intermediate dimer of xylylene ([2,2']paracyclophane) and derivatives related to that compound and general structure. Also, a general method for the formation of cyclophanes, and related compounds with various substituents, via a low cost method is desired. Also needed is an improved method to apply the xylylene (or substituted xylylene) monomers to make coatings and other polymer products derived from this reactive intermediate.

It is therefore an object of this invention to alleviate the costs and problems described in the known processes described above. First a general method for the formation of the reactive intermediate xylylene is shown. Secondly, a method whereby the formation of the stable intermediate chemical compound such as [2,2']paracyclophane ("the dimer"), and related structures, is shown for utility in existing manufacturing processes. Third, it is also shown to describe a direct and economical method for the application of the monomer to the target without the need for reduced pressure, or any pressure change for that matter.

In a preferred embodiment of the invention an apparatus and method to form the reactive intermediate p-xylylene through the use of a heated a pyrolysis reaction tube into which a flowing stream of a mixture of inert gas and nitrous oxide with xylene vapor in an inert carrier gas at atmospheric pressure with the exit gases nonvolatile reaction products being condensed onto a cooled vessel is disclosed.

In another embodiment, an apparatus and method to mix cool nonreactive gases into the hot reaction stream, resulting in cooling of the elevated temperature of the reaction gases and thus improving the ability of the reactive intermediate to condense and adhere to the surface, is disclosed.

In another embodiment, an apparatus and method to have the reaction proceed at an increased pressure and an expansion value at the exit of the heated pyrolysis reaction tube to provide expansion cooling of the hot gases below their inversion temperatures by the Joule-Thomson effect is disclosed.

In another embodiment, an apparatus and method using organic starting materials with substituents including chloro, dichloro, methoxy, and methyl are disclosed.

In another embodiment, an apparatus and method for using organic starting materials with meta and/or ortho orientation of the substituents on the aromatic rings is disclosed.

In another embodiment, an apparatus and methods for the indirect radical formation and/or ionization of the starting material through the reaction of the starting material (e.g. p-xylene) with a plasma and/or combination heating source is disclosed.

In another embodiment, substitution of nitrogen for argon and/or other essentially inert gases is disclosed. 1

DETAILED DESCRIPTION

Figure 1:
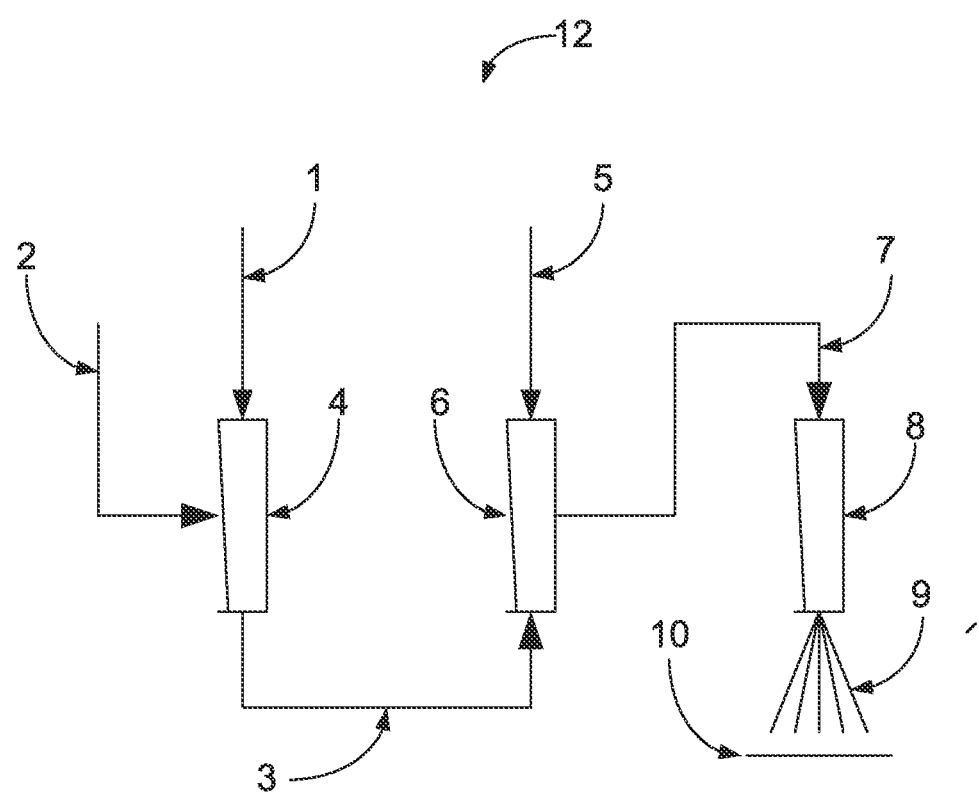
FIG. 1 is a schematic drawing of the basic apparatus for producing reaction 1.

Apparatus Description for Reaction 1:
Now referencing FIG. 1 where starting material feed 1 is introduced into chamber 4 by utilization of a pumping mechanism (not shown) for liquid or solid feeds.
Typically chamber 4 would be a heated tube or other evaporation device to volitilize starting material feed 1.
Starting material feed 1 is evaporated and mixed with inert gas 2 in chamber 4. Inert gas 2 may be any of a group of inert gases such as but not limited to Argon.
The resulting volatile mixture 3 is transported to chamber 6 and subsequently mixed with nitrous oxide 5, to produce chemical reaction mixture 7.
Reaction chamber 8 is typically heated to approximately 450° C. to 800° C. to enable the reaction and allow the vaporization of the reaction products to be expelled as products 9, onto collection surface 10.

Figure 2:
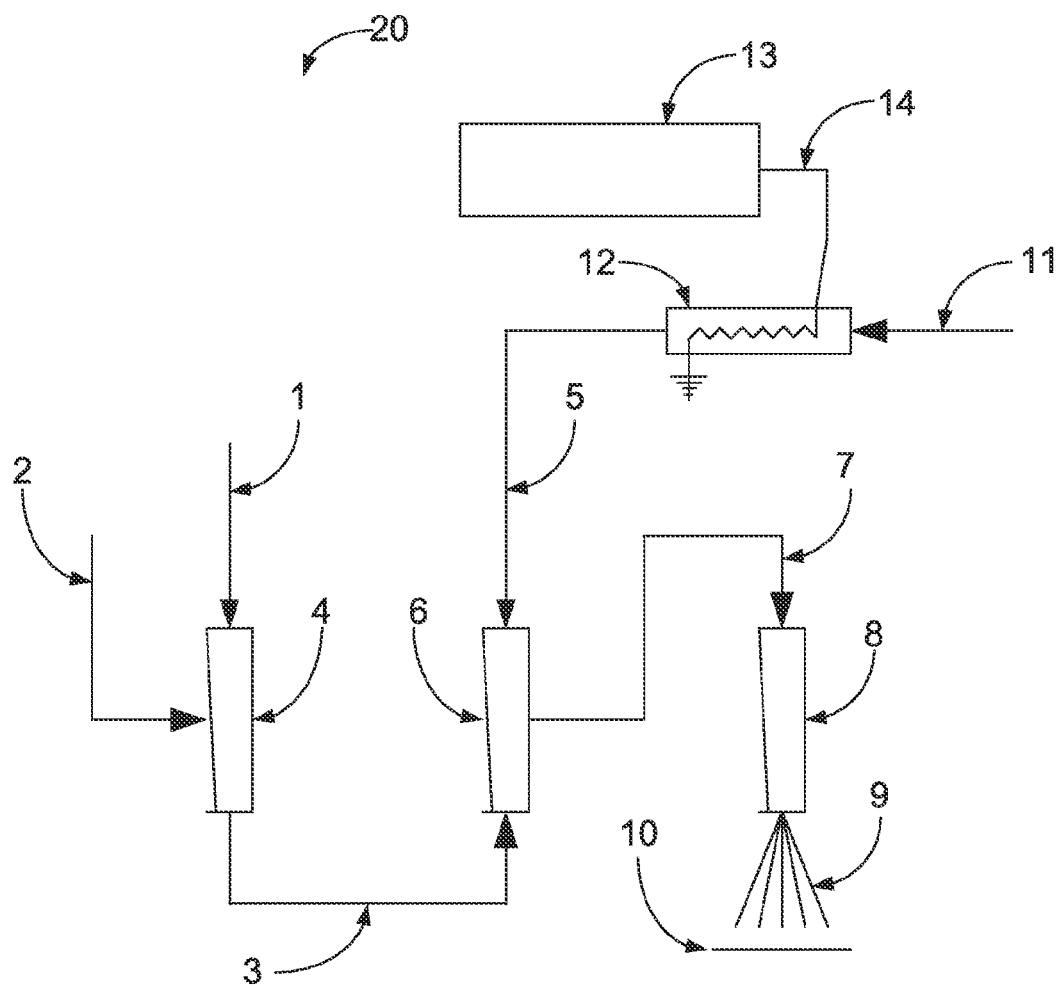
FIG. 2 is a schematic drawing of the basic apparatus for producing reaction 2.

Apparatus Description for Reaction 2:
Now referencing FIG. 2 where starting material feed 1 is introduced into chamber 4 by utilization of a pumping mechanism (not shown) for liquid or solid feeds.
Typically chamber 4 would be a heated tube or other evaporation device to volitilize starting material feed 1.
Starting material feed 1 is evaporated and mixed with inert gas 2 in chamber 4. Inert gas 2 may be any of a group of inert gases such as but not limited to Argon.
The resulting volatile mixture 3 is transported to chamber 6.
The formation of the gaseous plasma 5, is from chamber 12, that is electrically connected via conductor 14 to electrical plasma generator 13. Gas feed 11 is a feed of a suitable gas for conversion to gaseous plasma 5 by induction into chamber 12 resulting in gaseous plasma 5.

Volatile mixture 3 is subsequently mixed with gaseous plasma 5 in chamber 6 to produce chemical reaction mixture 7 which is transported to reaction chamber 8.

Reaction chamber 8 is typically heated to approximately 450° C. to 800° C. to enable the reaction and to allow the vaporization of the reaction products to be expelled as products 9, onto collection surface 10.

Reaction 1:

To form the reactive intermediate p-xylylene, a pyrolysis reaction tube was constructed. The main element in the heated area was an Inconel (nickel alloy 600) tube (0.325" OD×0.277" ID×60" length, Grainger #3ACP8). The tube was electrically heated to the indicated temperatures. A flowing stream of argon gas mixture comprised of nitrous oxide (Airgas # UM1070) with xylene vapor (Aldrich #134449-4L) in the carrier gas of argon (Airgas#UM 1006) was introduced to the tube at a total flow rate of 20 to 100 mL/minute at a temperature of 450° C. to 630° C. and at atmospheric pressure. The ratio of gases is adjusted to provide approximately molar stoichiometric ratios of 1:1 (xylene to nitrous oxide). The exit gas was comprised of a clear colorless flow of reactive gas. Condensation of the gas onto a cooled glass vessel resulted in the deposition of a colorless to cream colored solid. This solid is soluble in 95% ethanol. The solid was compared to a sample of [2,2']paracyclophane (Aldrich #P225-5G-A) by TLC analysis (15% ethyl acetate in hexane on silica plates) and was shown to give identical rf.

In this reaction it is presumed, but not proven, that the reactive p-xylylene reactive intermediate is formed and subsequently dimerized in the reaction tube or during condensation onto the glass container. This reaction used to synthesize the dimer, in comparison with the known "Gorham process", results in a vast improvement in the overall synthesis yield of the dimer and also results in a vast improvement in the purity of the dimer directly from the reaction. It is understood that variation in the stoichiometric amounts of the reactants may be adjusted to provide for greater or lesser yield with associated purities varying to provide a more economical process or better overall production efficiency without substantially deviating from the scope of this invention. Subsequent purifications of the materials from this reaction can be performed on this material in a manner that is much easier to accomplish than with previously taught processes.

The reaction is shown below.

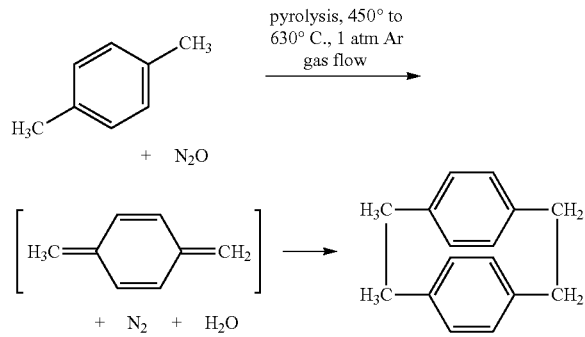

As the reaction temperature is increased to >650° C., the deposition of the xylylene monomer can proceed directly onto a solid substrate target without the necessity for isolation of the intermediate dimer. Deposition of the exit gas at above 650° C. reaction temperature upon a cool glass plate resulted in formation of an ethanol insoluble substance that displays characteristics of a parylene polymer. However, solubility characteristics clearly show that the material is insoluble in all common solvents (i.e. hexane, xylene, ethyl acetate, ethanol, water).

Increased amounts of nitrous oxide results in partial and/or complete oxidation of xylene with reduced formation of the desired cyclophane or its polymer. Close control of the stoichiometry is desired in this gas phase reaction.

Cooling of the elevated temperature gases exiting from the reaction tube is necessary. If the reaction gas is at too high of a temperature, the ability of the reactive intermediate to condense and adhere to a surface is greatly reduced. To this end, a device to mix cool nonreactive gases into the hot reaction stream has been devised. Additionally, the reaction may proceed at increased pressure (above atmospheric pressure), and an expansion valve may be used at the exit of the reaction to provide Joule-Thomson effect cooling of the hot gas when the gas is below its inversion temperature.

The method may be extended to other substrates such as the ones shown below.

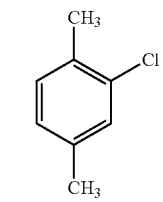
2-CHLORO-1,4-DIMETHYLBENZENE

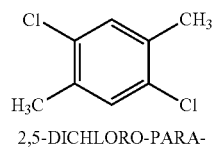
2,5-DICHLORO-PARA-XYLENE

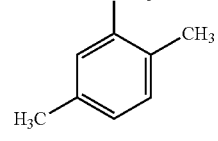
2,5-DIMETHYLANISOLE

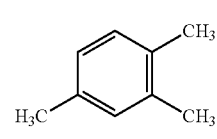
1,2,4-TRIMETHYLBENZENE

It should be noted that substituents such as the ones noted above (chloro, dichloro, methoxy, and methyl) are not the only aromatic substituents that are capable of being modified by this process into reactive intermediates and their subsequent polymers. Additionally, the paracyclophanes and compounds derived thereof are not exclusive to this process. Meta and ortho orientation of the substituents on the aromatic rings are also viable reaction starting materials. The reaction can be generalized to include all compounds that are capable of reaction with nitrous oxide or its intermediate reaction products and also contain hydrogen atoms stabilized by the presence of an aromatic ring. Typically such hydrogen atoms are located in a position alpha to a phenyl ring (benzylic position). Micheal structures removed from the alpha aromatic ring positions are known to give similar reactivity to the hydrogen alpha to the aromatic ring position as is well known to those versed in organic synthesis. However, the reactivity of such hydrogen atoms is not limited to alpha and/or Michael positions from an aromatic ring or the aromatic ring such as benzene. Other aromatic stabilizations are known for many different rings, fused rings, and non-ring systems, as known to those versed in the art of organic Chemistry. Such starting materials may preferably have the presence of two hydrogen atoms that are capable of being removed to form partially oxidized starting materials. These preferred materials may optionally have the ability to dimerize, trimerize, oligiomerize, or polymerize. The example used in this invention is p-xylene.

Alternatively, a plasma gas can be used with the aforementioned starting materials to form the intermediate oxidized products that may subsequently react to form reaction products that are oxidized forms of the starting materials which may be monomers, dimers, trimers, oligiomers, or polymers.

Treating the reactive surfaces that may contact the products of these reactions using plasma cleaning of the surface prior to exposure to the reactive intermediate is well known. However, that process is incidental to this method of forming the chemical compounds necessary for the coating or polymer.

A method for the formation of plasma is well documented and known to those familiar in the art of plasma formation. An example, Reaction 2, of such a plasma reaction utilizing the method similar to described in Reaction 1, is another embodiment for this general method.

Since the reaction is similar for all compounds claimed for this method, the use of p-xylene will be used for discussion purposes. It is clear to those versed in the art of Chemistry that the utilization of similar compounds would give similar results, and therefore exhaustive discussion of structural differences in reactivity would add little, if anything, to the teachings of this discovery.

Reaction 2:

To a quartz tube of 3/8" diameter and 12" long is attached a 1/16" 316 stainless steel tube connected to a gaseous source (such as argon or nitrogen). The stainless steel tube is positioned such that it is a short distance from a grounded electrode (approximately 5 mm to 15 mm). A plasma generator (InfoUnlimited PVM-400, to 50 kHz, 0 to 6000V) is connected to the 1/16" tube and the grounded electrode. The grounded electrode is positioned and connected such that the gases after having passed over the grounded electrode are allowed to mix with an argon/p-xylene mixture. The resultant mixture is allowed to pass through a 3/8" diameter×12" tube at a temperature ranging from ambient to 800° C. The electric power is supplied to the generator sufficient to allow reaction of the xylene or other starting materials to proceed mostly to completion. Full reaction of the starting material is not necessary. At lower temperatures (ambient to 500° C.), a solid is formed in the exit tube. At high temperatures (500 to 650° C.) the output of the tube can be mixed with cooling gases and/or directed to a cooled solid or liquid target to condense dimer. At even higher temperatures (650 to 800° C.) the output of the tube can be mixed with cooling gases and/or directed to a cooled solid or liquid target to condense monomer. Subsequent polymerization of the condensed monomer is likely to occur rapidly.

Substitution of nitrogen for argon and/or other essentially inert gases are possible without substantially deviating from this procedure. Additionally, modification of the electrode polarity, electrode materials, containment material, and temperatures are possible without significant deviation from the scope of this invention.

Since condensation of the "monomer" of p-xylene is difficult due to the high temperatures of the reaction, it is advantageous to add cool inert gases to the reaction products. Methods for doing this are very simple and well known.

In place of the cool gas method for cooling the reaction products, there is some advantage to allowing the reaction to proceed at a higher pressure and allowing the reaction products to expand into a lower pressure environment. Joule-Thomson cooling occurs, and the reaction products are very rapidly cooled. Subsequent condensation onto the target can then take place with a lower heat load on the target.

What is claimed is:

1. A method for producing dimers, oligomers, and polymers from the oxidation of a hydrogen atom alpha to an aromatic ring comprising:
   a. the introduction of an organic starting material containing at least one hydrogen atom alpha to an aromatic ring into a flowing stream of gas;
   b. said gas is subsequently mixed with nitrous oxide;
   c. a reaction between said hydrogen atom to an aromatic ring and said flowing stream of gas is then heated to a reaction temperature to allow oxidation of the alpha hydrogen and subsequent formation of monomers, dimers, oligomers, or polymers depending on said temperature.

2. A method as in claim 1 where there are two hydrogen atoms alpha to the same aromatic ring.

3. A method as in claim 1 where the aromatic ring is benzene.

4. A method as in claim 1 where the aromatic ring is not a benzene.

5. A method as in claim 1 where the output of the reaction is mixed with cool inert gases.

6. A method as in claim 1 where the output of the reaction is attached to a back pressure device to allow higher pressure in the reaction.

7. A method for the production of dimers, oligomers, and polymers from the oxidation of a hydrogen atom alpha to an aromatic ring comprising:
   a. introduction of an organic starting material containing at least one hydrogen atom alpha to an aromatic ring into a flowing stream of gas;
   b. said flowing stream of gas is subsequently mixed with a plasma gas forming a reaction mixture;
   c. said reaction mixture is then heated to a reaction temperature to allow oxidation of the alpha hydrogen and subsequent formation of monomers, dimers, oligomers, or polymers.

8. A method as in claim 7 where two hydrogen atoms alpha to the same aromatic ring.

9. A method as in claim 7 where the aromatic rings is benzene.

10. A method as in claim 7 where the aromatic ring is not benzene.

11. A method as in claim 7 where the output of the reaction mixture is mixed with cool inert gases.

12. A method as in claim 7 where the output of the final reaction is attached to a back pressure device to allow the reaction to occur at a higher pressure.

* * * * *